United States Patent [19]

Mukai et al.

[11] Patent Number: 5,151,479
[45] Date of Patent: Sep. 29, 1992

[54] DENTAL ADHESIVE COMPOSITION

[75] Inventors: Nobuhiro Mukai; Hitoshi Ige; Takayuki Makino; Junko Atarashi, all of Hiroshima, Japan

[73] Assignee: Mitsubishi Rayon Co., Ltd., Tokyo, Japan

[21] Appl. No.: 511,742

[22] Filed: Apr. 20, 1990

[30] Foreign Application Priority Data

Apr. 20, 1989 [JP] Japan .................................. 1-101291

[51] Int. Cl.$^5$ .................. C08F 230/02; C08F 220/34; A61K 6/10
[52] U.S. Cl. .................. 526/277; 526/328.5; 523/109
[58] Field of Search .................. 526/276, 277, 274; 523/109

[56] References Cited

U.S. PATENT DOCUMENTS 4,563,486 1/1986 Nemcek et al. .................. 523/115
4,816,495 3/1989 Blackwell et al. .................. 522/14

FOREIGN PATENT DOCUMENTS 2217989 8/1989 United Kingdom .

*Primary Examiner*—Joseph L. Schofer
*Assistant Examiner*—Wu C. Cheng
*Attorney, Agent, or Firm*—Cushman, Darby & Cushman

[57] ABSTRACT

This invention provides dental adhesive compositions consisting essentially of
(a) an aliphatic amine salt of a polymerizable phosphoric ester, as represented by the formula

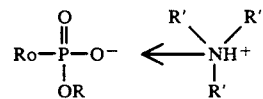

where R and R' are specific radicals;
(b) at least one radical-polymerizable unsaturated monomer; and
(c) a radical polymerization initiator. These compositions are useful in bonding living dental tissue restoration materials to living tooth tissues, particularly to dentin.

10 Claims, No Drawings

DENTAL ADHESIVE COMPOSITION

BACKGROUND OF THE INVENTION (a) Field of the Invention

This invention relates to dental adhesive compositions which have excellent bonding properties and are useful in bonding dental restoration materials (such as metals, organic polymers and ceramics) to living tooth tissues.

(b) Description of the Prior Art

In the field of dental materials, a variety of materials have conventionally been used for the purpose of restoring carious teeth, missing teeth and the like. Such materials include metals such as gold, silver, platinum, alloys and amalgam; organic polymeric matrials such as polymethyl methacrylate, polycarbonate, cured products of multifunctional vinyl monomers, and so-called composite resins comprising such polymers having fillers incorporated therein; and ceramic materials such as porcelain.

However, these materials are inherently hard to bond to living dental tissues.

Accordingly, in order to enhance the bonding properties between the above-described restorative materials and the constituents of the tooth tissues, including inorganic components such as calcium phosphate (e.g., hydroxyapatite) and organic components such as collagen, there have been proposed a number of dental adhesive compositions in which a compound having a phosphate, hydroxyl or acid anhydride group, such as 2-methacryloyloxyethylphenylphosphoric acid, 2-hydroxy-3-β-naphthoxypropyl methacrylate or 4-methacryloyloxyethyltrimellitic acid anhydride, is used as the adhesive component.

However, adhesives having the above-described functional group (i.e., a phosphate, hydroxyl or acid anhydride group) are generally poor in radical polymerizability at room temperature. Moreover, since dentin has a significantly higher protein content than enamel and contains a large number of dentinal tubules filled with a body fluid, adhesives having a polar group as described above are not suitable for use in bonding to dentin. In fact, it has often been the case that they exhibit no bonding power to dentin.

For these reasons, the above-described adhesives require pretreatment of the tooth apatite with an etching agent such as phosphoric acid.

However, even if such pretreatment is made, the above-described adhesives still fail to exhibit satisfactorily high bond strength. Moreover, the pretreatment cannot be continued for a longer period of time because it may be harmful to the tooth. Thus, if such an adhesive is used to bond a restorative material to a tooth, a gap will be produced between the restorative material and the dentin in a long period of time and, in the worst case, the restorative material may fall off.

OBJECT AND SUMMARY OF THE INVENTION

It is an object of the present invention to provide a dental adhesive composition which, when used to bond restorative materials to living tooth tissues, particularly to dentin, exhibits practically sufficient bonding power even in a severe environment within the oral cavity.

The above object of the present invention is accomplished by providing a dental adhesive composition consisting essentially of
- (a) an aliphatic amine salt of a polymerizable phosphoric ester;
- (b) at least one radical-polymerizable unsaturated monomer; and
- (c) a radical polymerization initiator.

The aliphatic amine salt of polymerizable phosphoric ester used in the dental adhesive composition of the present invention can be any compound in which a phosphoric ester having one or more polymerizable unsaturated bonds and a phosphate group is combined with an aliphatic amine to form a salt. However, it is preferable to use compounds of the general formula

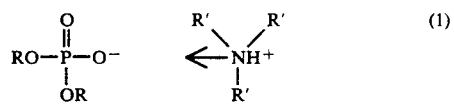

where R is $CH_2=CHCO_2(CH_2)_nO(CH_2)-$, $CH_2=C(CH_3)CO_2(CH_2)_n-$, $CH_2=CHCO_2(CH_2)_n-$, $CH_2=C(CH_3)CO_2(CH_2)_nO(CH_2)-$ or hydrogen, n is a whole number of 1 to 5; the two R radicals may be the same or different, but they should not be hydrogen at the same time; R' is a hydrocarbon radical having 1 to 5 carbon atoms or any of the radicals described above for R; and the three R' radicals may be the same or different, but they should not be hydrogen at the same time and should not contain an unsaturated bond at the same time.

These aliphatic amine salts of polymerizable phosphoric esters serve to produce a strong adhesion between living dental tissues and restorative materials.

DETAILED DESCRIPTION OF THE INVENTION

Specific examples of the aliphatic amine salts of polymerizable phosphoric esters represented by the above general formula (1) include the monoethanolamine, dimethylaminoethyl methacrylate and diethylaminoethyl methacrylate salts of (meth)acryloyloxyethyl phosphate, (meth)acryloyloxypropyl phosphate, (meth)acryloyloxyethyloxyethyl phosphate and bis[(meth)acryloyloxyethyl] phosphate. Especially preferred is methacryloyloxyethyl phosphate dimethylaminoethyl methacrylate salt.

The radical-polymerizable unsaturated monomer used in the dental adhesive compositions of the present invention can be a monofunctional or a multifunctional unsaturated monomer. Examples of useful monofunctional unsaturated monomers include methyl (meth)acrylate, ethyl (meth)acrylate, propyl (meth)acrylate, butyl (meth)acrylate, pentyl (meth)acrylate, hexyl (meth)acrylate, 2-hydroxyethyl (meth)acrylate, vinyl acetate, styrene, acrylonitrile, glycidyl methacrylate and benzyl methacrylate. Among others, methyl (meth)acrylate, benzyl methacrylate and 2-hydroxyethyl methacrylate are preferred.

Examples of useful multifunctional unsaturated monomers include ethylene glycol di(meth)acrylate, polyethylene glycol di(meth)acrylate having 2 to 20 ethylene glycol units, 1,6-hexanediol di(meth)acrylate, neopentyl glycol di(meth)acrylate, trimethylolpropane tri(meth)acrylate,

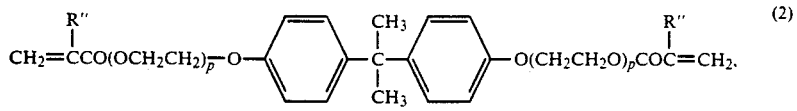

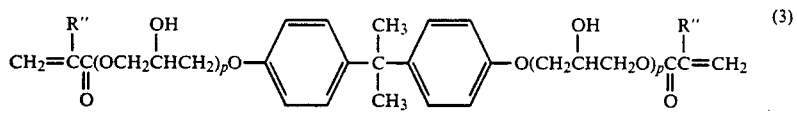

where R" is hydrogen or methyl, and p is a whole number of 1 to 20,

wherein $R^3$ is hydrogen or methyl and the two $R^3$ radicals may be the same or different, and X is an alkylene group of 1 to 6 carbon atoms or

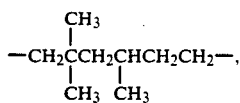

1,2-bis[3-meth)acryloyloxy-2-hydroxypropoxy]ethane and 1,4-bis[3-(meth)acryloyloxy-2-hydroxypropoxy]butane.

Among the foregoing radical-polymerizable unsaturated monomers, preferred monomers are methyl (meth)acrylate, benzyl methacrylate, 2-hydroxyethyl methacrylate, ethylene glycol di(meth)acrylate, triethylene glycol di(meth)acrylate, nonaethylene glycol di(meth)acrylate, tetradecaethylene glycol di(meth)acrylate, trimethylolpropane triacrylate, 1,6-hexanediol di(meth)acrylate, compounds of the general formula (2) or (3) in which R" is methyl, the compound of the general formula (4) in which all $R^3$ radicals are methyl and X is hexylene (hereinafter referred to as U-4H), and the compound represented by the following formula (hereinafter referred to as U-4HA).

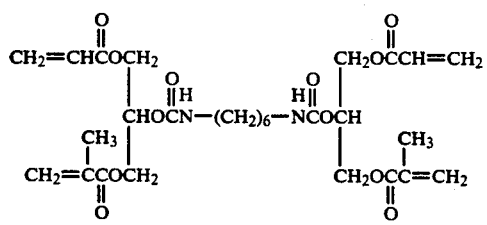

In the dental adhesive compositions of the present invention, the weight ratio of components (a) to component (b) should be such that compound (a) is preferably present in an amount of 0.1 to 30 parts by weight, more preferably 0.5 to 10 parts by weight and most preferably 1.0 to 5.0 parts by weight, per 100 parts by weight of component (b).

The radical polymerization initiator used as component (c) in the dental adhesive compositions of the present invention may be a photopolymerization initiator or a redox polymerization initiator.

Where a photopolymerization initiator is used as the radical polymerization initiator, both ultraviolet light polymerization initiators and visible light polymerization initiators may be used. However, if the dental adhesive compositions of the present invention are to be used in the oral cavity, it is preferable that they contain a photopolymerization initiator capable of initiating the polymerization in response to visible light in the wavelength range of about 400 to 1,200 nm, because ultraviolet light may do harm to the oral mucosa. Accordingly, it is preferable to use a photopolymerization initiator which can be excited by visible light in the wavelength range of about 400 to 1,200 nm. The photopolymerization initiator may comprise a single photopolymerization initiator which exhibits hydrogen abstracting power when excited by light, or a combination of a so-called photosensitizer (i.e., a compound that is excited by light but does not exhibit hydrogen abstracting power) and a reducing agent. An example of the former is camphorquinone. In this case, however, a reducing agent may preferably be used in combination with the photopolymerization initiator to enhance its hydrogen abstracting power. In this situation, the photopolymerization initiator can be regarded as a photosensitizer. Examples of useful photosensitizers are -diketone compounds such as benzil and diacetyl. Among others, camphorquinone is preferably used because of its high polymerization activity.

Where a combination of a photosensitizer and a reducing agent is used in the dental adhesive compositions of the present invention, the reducing agent can be any compound that exhibits hydrogen abstracting power when it receives energy from the excited photosensitizer. As such reducing agents, tertiary amines are preferably used.

Examples of useful tertiary amines include aliphatic amines such as trimethylamine, triethylamine and tripropylamine; and aromatic amines such as isoamyl 4-(N,N-dimethylamino)benzoate, hexyl 4-(N,N-dimethylamino)benzoate, heptyl 4-(N,N-dimethylamino)benzoate, octyl 4-(N,N-dimethylamino)benzoate, 4,4'-bis(dimethylamino)benzophenone, 4,4'-bis(diethylamino)benzophenone and 4,4'-bis(dibutylamino)benzophenone. Among others, aromatic tertiary amines are preferred. In particular, a combination of camphorquinone as a photosensitizer and 4,4'-bis(diethylamino)benzophenone as a reducing agent is most preferred because of its excellent visible light polymerizing activity.

The appropriate amount of photopolymerization initiator added to the dental adhesive compositions of the present invention may vary according to the type of photopolymerization initiator or photosensitizer/reducing agent used. However, the photopolymerization initiator is usually added in an amount of 0.005 to 30% by weight based on the total amount of the radical-polymerizable unsaturated monomer(s). For example, in the camphorquinone/4,4'-bis(diethylamino)benzophenone system, camphorquinone is preferably added in an amount of 0.005 to 30% by weight, more preferably 0.03 to 20% by weight, based on the total amount of the radical-polymerizable unsaturated monomer(s), and 4,4'-bis-(diethylamino)benzophenone is preferably added in an amount of 0.01 to 25% by weight, more preferably 0.05 to 20% by weight.

Where a redox polymerization initiator is used in the dental adhesive compositions of the present invention, it preferably comprises a combination of an aromatic amine and an organic peroxide, a combination of a sulfinic acid salt and an organic peroxide, or a combination of an aromatic amine, a sulfinic acid salt and an organic peroxide. Examples of useful organic peroxides include diacetyl peroxide, dilauroyl peroxide, distearoyl peroxide, dibenzoyl peroxide and di-p-chlorobenzoyl peroxide. Among them, dibenzoyl peroxide is preferably used because of its excellent room temperature polymerizing activity.

As the aromatic amine, there may be used any of primary, secondary and tertiary amines. However, tertiary amines are preferably used from the viewpoint of room temperature polymerizing activity. Preferred examples of useful aromatic amines include, N,N-dimethylaniline, N,N-diethylaniline, N,N-di($\beta$-hydroxyethyl)aniline, N,N-dimethyl-p-toluidine, N,N-diethyl-p-toluidine, N,N-di($\beta$-hydroxyethyl)-p-toluidine, N-methylaniline, N-methyl-p-toluidine, N,N-dimethylanisidine, N,N-diethylanisidine and diphenylamine. Among them, N,N-dimethyl-p-toluidine and N,N-di($\beta$-hydroxyethyl)-p-toluidine are more preferred from the viewpoint of room temperature polymerizing activity.

Examples of useful sulfinic acid salts include sodium p-toluenesulfinate, sodium benzenesulfinate, potassium benzenesulfinate, calcium benzenesulfinate, barium benzenesulfinate and ammonium benzenesulfinate. Among them, sodium p-toluenesulfinate is preferably used from the viewpoint of room temperature polymerizing activity. Where a redox polymerization initiator is used the organic peroxide is preferably used in an amount of 0.01 to 10% by weight, more preferably 0.05 to 5% by weight, based on the total amount of the radical-polymerizable unsaturated monomer(s).

In order to control their viscosity from the viewpoint of workability, the dental adhesive composition of the present invention can contain low-boiling organic solvents such as ethanol, isopropanol and chloroform.

In addition, the dental adhesive compositions of the present invention can also contain inorganic fillers, organic polymers, colorants, polymerization inhibitors, antioxidants, ultraviolet light absorbers and the like, in commonly employed amounts.

Examples of useful inorganic fillers include silica powder, quartz powder and various glass powders; examples of useful organic polymers include polymethyl methacrylate and polystyrene; examples of useful colorants include various pigments and dyes; and examples of useful polymerization inhibitors include hydroquinone and methylphenol.

The dental adhesive compositions of the present invention contain at least the above-described components (a), (b) and (c), until use, these three components may be stored in a mixed state. However, where the dental adhesive composition of the present invention comprises a combination of components whose storage stability will be reduced during storage in a mixed state, it is also possible to store those components separately and mix them prior to use. For example, where a redox polymerization initiator is used, it is possible to divide component (b), namely a radical-polymerizable unsaturated monomer or monomers, into two parts, add an organic peroxide to one part, and add an aromatic amine or a sulfinic acid salt to the other. These two parts may be stored separately and mixed prior to use.

In the dental adhesive compositions of the present invention, a redox polymerization initiator and a photopolymerization initiator may be used in combination.

The dental adhesive compositions of the present invention can be applied to a variety of restorative materials. Insofar as materials to be bonded to dentin are concerned, they have excellent bonding properties to thermosetting resins for use in composite resins (i.e., composite materials obtained by blending a multifunctional monomer with an inorganic filler) and crown resins; thermoplastic resins for use in denture bases, such as polymethyl methacrylate, polysulfone and polycarbonate; inorganic materials such as various cementing materials, amalgam, alumina, gold, and alloys; and the like.

The present invention is further illustrated by the following examples. However, these examples are not to be construed to limit the scope of the invention.

| Preparation of restorative material A (visible light curable composite resin) | |
|---|---|
| Ingredient | Amount |
| 2,2-Bis[4-methacryloyloxyethoxy)phenyl]-propane (hereinafter referred to as Bis-MEPP) | 8 g |
| Triethylene glycol dimethacrylate (hereinafter referred to as TEGDMA) | 12 g |
| Silane-treated quartz powder (comprising quartz powder to which 2% by weight of $\gamma$-methacryloyloxypropyl trimethoxy silane has been added, and having an average particle diameter of about 4 $\mu$m) | 74 g |
| Finely powdered silicon dioxide (#R-972, manufactured by Nippon Aerosil Co., Ltd.) | 6 g |
| Camphorquinone | 0.4 g |
| Isoamyl 4-(N,N-dimethylamino)benzoate | 2 g |

According to the above formulation, multifunctional monomer, inorganic fillers and visible light polymerization initiators were blended in a dark room to obtain a visible light curable composite resin (hereinafter referred to as restorative material A).

| Preparation of restorative material A (visible light curable composite resin) | |
|---|---|
| Ingredient | Amount |
| 2,2-Bis[4-(3-methacryloyloxy-2-hydroxypropoxy)phenyl]propane (hereinafter referred to as Bis-GMA) | 40 g |
| TEGDMA | 60 g |
| Camphorquinone | 0.7 g |
| Isoamyl 4-(N,N-dimethylamino)benzoate | 2.8 g |

According to the above formulation, multifunctional monomers and visible light polymerization initiators were blended in a dark room to obtain a visible light curable crown resin (hereinafter referred to as restorative material B).

| Preparation of restorative material C (redox polymerization type composite resin) | |
|---|---|
| Ingredient | Amount |
| (Catalyst paste) | |
| Bis-GMA | 8 g |
| TEGDMA | 12 g |

-continued

| Preparation of restorative material C (redox polymerization type composite resin) | |
|---|---|
| Ingredient | Amount |
| Silane-treated quartz powder (same as used in restorative material A) | 74 g |
| Finely powdered silicon dioxide (same as used in restorative material A) | 6 g |
| Benzoyl peroxide | 2 g |
| (Base paste) | |
| Bis-GMA | 8 g |
| TEGDMA | 12 g |
| Silane-treated quartz powder (same as used in restorative material A) | 74 g |
| Finely powdered silicon dioxide (same as used in restorative material A) | 6 g |
| Dihydroxyethyl-p-toluidine | 4 g |

According to the above formulations, various ingredients were blended to obtain a catalyst paste and a base paste. These pastes were stored separately.

PROCEDURES FOR THE EVALUATION OF BONDING PROPERTIES OF DENTAL ADHESIVE COMPOSITIONS

The bonding properties of a dental adhesive composition using a photopolymerization initiator were evaluated according to the following procedure.

(1) Freshly extracted cattle fore-teeth were cut with a precision cutter (Isomet; manufactured by Bühler AG) to expose a flat enamel or dentin surface. Then, using a piece of No. 1000 water-resistant abrasive paper, the exposed surface was fully polished under a stream of water.

(2) The polished surfaces of the above specimens were treated with an etchant (manufactured by GC Dental Industries Co., Ltd.), washed with water, and then air-dried.

(3) A dental adhesive composition to be tested was applied to the polished and etched surface of each specimen. When the composition contained any volatile component such as solvent, it was evaporated and expelled by exposure to a stream of air for about 10 seconds.

(4) A cylindrical silicone ring (openable on one side) having an inner diameter of about 5 mm, a height of about 5 mm and a wall thickness of about 3 mm was placed on the surface to which the dental adhesive composition had been applied. Then, the silicone ring was filled with a liquid restorative material to a height of about 3 mm.

(5) The aperture of a visible light projector (GC Light: manufactured by GC Dental Industries Co., Ltd.) was brought into contact with the upper end of the silicone ring filled with the restorative material. Thus, the restorative material and the adhesive composition were cured by exposure to visible light for 60 seconds. After the lapse of about 10 minutes, the silicone ring was removed to obtain a specimen having the restorative material bonded to the enamel or dentin surface.

(6) After the entire specimen was stored in water at 37° C. for one day, a rod formed of methyl methacrylate resin and having the same diameter as the restorative material was joined to the top of the restorative material by means of a rapid-polymerizable resin (Uni Fast; manufactured by GC Dental Industries Co., Ltd.). The resulting assembly was subjected to a tensile test for the measurement of bond strength. The measuring conditions were as follows.

Tensile tester: Tensilon (manufactured by Toyo Boldwin Co., Ltd.).
Crosshead speed: 0.5 mm/min.
Full scale: 20 kgW.

The bonding properties of a dental adhesive composition using a redox polymerization initiator were evaluated in the same manner as described above, except that the dental adhesive composition was prepared by mixing fluids A and B immediately before use and the restorative material was prepared by mixing the catalyst paste and base paste of restorative material C immediately before use and kneading the mixture for 30 seconds. More specifically, freshly extracted cattle fore-teeth were cut, polished, etched, washed with water, and then dried as described in steps (1) and (2) above. Then, the dental adhesive composition was applied to each specimen as described in step (3) above, and a silicone ring was placed thereon and filled with restorative material C as described in step (4) above. After the assembly was allowed to stand at room temperature for 10 minutes, the silicone ring was removed to obtain a specimen having the restorative material bonded to the enamel or dentin surface.

The bond strength of the dental adhesive composition was measured in the same manner as described for photopolymerizable adhesive compositions.

EXAMPLES 1 to 9

The aliphatic amine salts of polymerizable phosphoric esters, radical-polymerizable unsaturated monomers and visible light polymerization initiators listed in Table 1 were blended with a general-purpose mixer in a dark room to obtain various dental adhesive compositions.

Using each of these dental adhesive compositions, restorative material A was bonded to enamel and dentin surfaces, and the resulting bond strengths were measured. The results thus obtained are shown in Table 2.

TABLE 1

| Example No. | Amounts of radical-polymerizable unsaturated monomers (g) | | | | | Aliphatic amine salt of phosphoric ester (g) | | Amounts of polymerization initiators used (g) | |
|---|---|---|---|---|---|---|---|---|---|
| | HEMA (*1) | TEGDMA | Bis-GMA | Bis-MEPP | U-4HA | | | Camphorquinone | Tertiary amine (*6) |
| 1 | 20 | 40 | 60 | — | — | (*2) | 2.0 | 0.8 | 1.2 |
| 2 | 20 | — | 20 | 60 | — | (*2) | 2.0 | 0.8 | 1.2 |
| 3 | 20 | — | 20 | | 60 | (*2) | 2.0 | 0.8 | 1.2 |
| 4 | 20 | 20 | 20 | | 40 | (*2) | 2.0 | 0.8 | 1.2 |
| 5 | 20 | 20 | 20 | | 40 | (*2) | 1.0 | 0.8 | 1.2 |
| 6 | 20 | 20 | 20 | | 40 | (*2) | 5.0 | 0.8 | 1.2 |
| 7 | 20 | 20 | 20 | | 40 | (*3) | 2.0 | 0.8 | 1.2 |
| 8 | 20 | 20 | 20 | | 40 | (*4) | 2.0 | 0.8 | 1.2 |

TABLE 1-continued

| Example No. | Amounts of radical-polymerizable unsaturated monomers (g) | | | | | Aliphatic amine salt of phosphoric ester (g) | Amounts of polymerization initiators used (g) | |
|---|---|---|---|---|---|---|---|---|
| | HEMA (*1) | TEGDMA | Bis-GMA | Bis-MEPP | U-4HA | | Camphor-quinone | Tertiary amine (*6) |
| 9 | 20 | 20 | 20 | | 40 | (*5) 2.0 | 0.8 | 1.2 |

(*1) 2-Hydroxyethyl methacrylate
(*2) Methacryloyloxyethyl phosphate dimethylaminoethyl methacrylate
(*3) Methacryloyloxyethyl phosphate diethylaminoethyl methacrylate
(*4) Methacryloyloxypropyl phosphate dimethylaminoethyl methacrylate
(*5) Methacryloyloxyethyl phosphate monoethanolamine
(*6) 4,4-Bis(diethylamino)benzophenone

TABLE 2

| Example No. | Bond strength (kg/cm$^2$) | |
|---|---|---|
| | Enamel | Dentin |
| 1 | 215 | 45 |
| 2 | 224 | 31 |
| 3 | 209 | 52 |
| 4 | 237 | 68 |
| 5 | 217 | 55 |
| 6 | 240 | 51 |
| 7 | 231 | 48 |
| 8 | 201 | 41 |
| 9 | 214 | 43 |

EXAMPLES 10 to 12

Dental adhesive compositions were prepared in the same manner as in Example 1, except that the radical-polymerizable unsaturated monomers, aliphatic amine salt of polymerizable phosphoric ester, and visible light polymerization initiators listed in Table 3 were used. Then, the bond strengths of these compositions were measured in the same manner as in Example 1. The results thus obtained are shown in Table 4.

TABLE 3

| Example No. | Amounts of radical-polymerizable unsaturated monomers (g) | | | | Aliphatic amine salt of phosphoric ester (g) | Amounts of polymerization initiators used (g) | |
|---|---|---|---|---|---|---|---|
| | Vinyl acetate | Styrene | HEMA (*1) | Bis-GMA | | Camphor-quinone | Tertiary amine (*6) |
| 10 | 10 | 10 | 20 | 60 | (*2) 2.0 | 0.8 | 1.2 |
| 11 | 20 | — | 30 | 50 | (*2) 2.0 | 0.8 | 1.2 |
| 12 | — | 20 | 30 | 50 | (*2) 2.0 | 0.8 | 1.2 |

TABLE 4

| Example No. | Bond strength (kg/cm$^2$) | |
|---|---|---|
| | Enamel | Dentin |
| 10 | 198 | 45 |
| 11 | 205 | 43 |
| 12 | 190 | 35 |

EXAMPLE 13

| Ingredient | Amount |
|---|---|
| [Radical-polymerizable unsaturated monomer/redox polymerization initiator mixture (1-A)] | |
| U-4HA | 20 g |
| Triethylene glycol dimethacrylate | 10 g |
| Bis-GMA | 50 g |
| 2-Hydroxyethyl methacrylate | 20 g |
| Methacryloyloxyethyl phosphate dimethylaminoethyl methacrylate | 2.0 g |
| Dibenzoyl peroxide | 1.0 g |
| 2,6-Di-tert-butyl-4-methylphenol | 0.05 g |
| [Radical-polymerizable unsaturated monomer/redox polymerization initiator mixture (1-B)] | |

-continued

| Ingredient | Amount |
|---|---|
| 2-Hydroxyethyl methacrylate | 10 g |
| Ethanol | 90 g |
| Dihydroxyethyl-p-toluidine | 0.8 g |
| Sodium p-toluenesulfinate | 0.5 g |

The above mixtures (1-A) and (1-B) were separately prepared by blending the ingredients with a mixer in a dark room, and mixed immediately before use. When measured according to the procedure for the evaluation of dental adhesive compositions using a redox polymerization initiator, the bond strengths to enamel and dentin of this dental adhesive composition after storage in water for one day were 231 kg/cm$^2$ and 49 kg/cm$^2$, respectively.

EXAMPLES 14 to 17

Using the dental adhesive composition obtained in Example 1, its bonding properties to various restorative materials was evaluated in the same manner as in Example 1. The results thus obtained are shown in Table 5.

TABLE 5

| Example No. | Restorative material | Mean bond strength to enamel (kg/cm$^2$) | Mean bond strength to dentin (kg/cm$^2$) |
|---|---|---|---|
| 14 | Restorative material B | 198 | 43 |
| 15 | Commercially available one-part composite resin (*7) | 242 | 38 |
| 16 | Commercially available two-part composite resin (*8) | 214 | 41 |
| 17 | Polymethyl methacrylate (*9) | 227 | 50 |

(*7) Occlusin (manufactured by ICI Co., Ltd.)
(*8) Microrest AP (manufactured by GC Dental Industries Co., Ltd.).
(*9) Acrypet #VH (manufactured by Mitsubishi Rayon Co., Ltd.).

COMPARATIVE EXAMPLES 1 AND 2

In the same manner as in Example 13, two dental adhesive compositions containing no aliphatic amine salt of polymerizable phosphoric ester were prepared according to the following formulations (the combination of 2-A and 2-B and the combination of 3-A and 3-B.

Then, the bonding properties of these compositions was evaluated in the same manner as in Example 13.

| Ingredient | Amount |
| --- | --- |
| (2-A) | |
| U-4HA | 20 g |
| Triethylene glycol dimethacrylate | 10 g |
| Bis-GMA | 50 g |
| 2-Hydroxyethyl methacrylate | 20 g |
| Methacryloyloxyethyl phosphate | 2.0 g |
| Dibenzoyl peroxide | 1.0 g |
| (2-B) | |
| 2-Hydroxyethyl methacrylate | 10 g |
| Ethanol | 90 g |
| Dihdyroxyethyl-p-toluidine | 0.8 g |
| Sodium p-toluenesulfinate | 0.5 g |
| (3-A) | |
| U-4HA | 20 g |
| Triethylene glycol dimethacrylate | 10 g |
| Bis-GMA | 50 g |
| 2-Hydroxyethyl methacrylate | 20 g |
| Dimethylaminoethyl methacrylate | 2.0 g |
| Dibenzoyl peroxide | 1.0 g |
| (3-B) | |
| 2-Hydroxyethyl methacrylate | 10 g |
| Ethanol | 90 g |
| Dihydroxyethyl-p-toluidine | 0.8 g |
| Sodium p-toluenesulfinate | 0.5 g |

When measured after storage in water for one day, the bond strengths of dental adhesive composition 2 (the combination of 2-A and 2-B) to enamel and dentin were 184 kg/cm$^2$ and 25 kg/cm$^2$, respectively. Similarly, the bond strengths of dental adhesive composition 3 (the combination of 3-A and 3-B) to enamel and dentin were 107 kg/cm$^2$ and 10 kg/cm$^2$, respectively.

What is claimed is:

1. A dental adhesive composition consisting essentially of
   (a) an aliphatic amine salt of a polymerizable phosphoric ester represented by the following formula

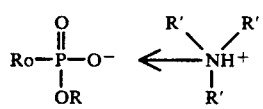

where R is CH$_2$=CHCO$_2$(CH$_2$)$_n$O(CH$_2$)—, CH$_2$=C(CH$_3$)CO$_2$(CH$_2$)$_n$—, CH$_2$=CHCO$_2$(CH$_2$)$_n$—, CH$_2$=C(CH$_3$)CO$_2$)(CH$_2$)$_n$O(CH$_2$)— or hydrogen, n is a whole number of 1 to 5, the two R radicals are not hydrogen at the same time, R' is a hydrocarbon radical having 1 to 5 carbon atoms or any of the radicals described above for R, the three R' radicals are not all hydrogen at the same time, the three R' radicals do not all contain an unsaturated bond at the same time;
   (b) at least one radical-polymerizable unsaturated monomer, and
   (c) a radical polymerization initiator.

2. A dental adhesive composition as claimed in claim 1 wherein the aliphatic amine salt of polymerizable phosphoric ester (a) is used in an amount of 0.1 to 30 parts by weight per 100 parts by weight of the radical-polymerizable unsaturated monomer (b).

3. A dental adhesive composition as claimed in claim 1 wherein the radical polymerization initiator is a photopolymerization initiator.

4. A dental adhesive composition as claimed in claim 1 wherein the radical polymerization initiator is a redox polymerization initiator.

5. A dental adhesive composition as claimed in claim 3 wherein the photopolymerization initiator is used in an amount of 0.005 to 30% by weight based on the radical-polymerizable unsaturated monomer.

6. A dental adhesive composition as claimed in claim 4 wherein the redox polymerization initiator comprises a combination of an aromatic amine and an organic peroxide, a combination of a sulfinic acid salt and an organic peroxide, or a combination of an aromatic amine, a sulfinic acid salt and an organic peroxide, and the organic peroxide is used in an amount of 0.01 to 10% by weight based on the radical-polymerizable unsaturated monomer.

7. A dental adhesive composition as claimed in claim 1 wherein the aliphatic amine salt of polymerizable phosphoric ester is a monoethanolamine, dimethylaminoethyl methacrylate or diethylaminoethyl methacrylate salt of (meth)acryloyloxyethyl phosphate, (meth)acryloyloxypropyl phosphate, (meth)acryloyloxyethyloxyethyl phosphate or bis phosphate.

8. A dental adhesive composition as claimed in claim 1 wherein the aliphatic amine salt of polymerizable phosphoric ester is methacryloyloxyethyl phosphate dimethylaminoethyl methacrylate.

9. A dental adhesive composition as claimed in claim 1 wherein the radical-polymerizable unsaturated monomer is a compound selected from the group consisting of the compound having the formula

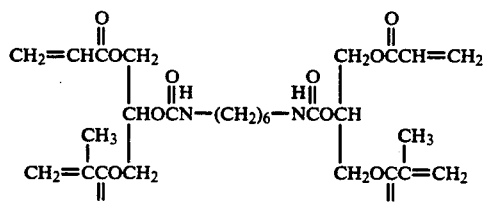

2,2-bis propane, triethylene glycol dimethacrylate, 2,2-bis propane and 2-hydroxyethyl methacrylate.

10. A dental adhesive composition as claimed in claim 3 wherein the radical polymerization initiator is a visible light polymerization initiator comprising a combination of camphorquinone and a tertiary amine.

* * * * *